(12) United States Patent
Xie et al.

(10) Patent No.: US 7,375,256 B2
(45) Date of Patent: May 20, 2008

(54) CATALYTIC CONVERSION PROCESS FOR PRODUCING LIGHT OLEFINS WITH A HIGH YIELD PETROLEUM HYDROCARBONS

(75) Inventors: Chaogang Xie, Beijing (CN); Jun Long, Beijing (CN); Jiushun Zhang, Beijing (CN); Zaiting Li, Beijing (CN); Xieqing Wang, Beijing (CN)

(73) Assignee: China Petroleum & Chemical Corporation, Beijing (CN)

( * ) Notice: Subject to any disclaimer, the term of this patent is extended or adjusted under 35 U.S.C. 154(b) by 536 days.

(21) Appl. No.: 10/878,187

(22) Filed: Jun. 29, 2004

(65) Prior Publication Data

US 2005/0020867 A1    Jan. 27, 2005

(30) Foreign Application Priority Data

Jun. 30, 2003   (CN) ............................... 03 1 47977
Jun. 30, 2003   (CN) ............................... 03 1 47978

(51) Int. Cl.
*C07C 4/06* (2006.01)
(52) U.S. Cl. .................... 585/652; 585/651; 585/650; 585/649; 585/653
(58) Field of Classification Search ............... 585/652, 585/651, 650, 649, 653
See application file for complete search history.

(56) References Cited

U.S. PATENT DOCUMENTS

| | | | |
|---|---|---|---|
| 3,578,403 A | 5/1971 | Moore | |
| 4,365,104 A | 12/1982 | Kaeding | |
| 4,980,053 A | 12/1990 | Li et al. | |
| 5,236,880 A | 8/1993 | Chapman | |
| 5,318,696 A | 6/1994 | Kowalski | |
| 5,380,690 A | 1/1995 | Zhicheng et al. | |
| 5,414,075 A | 5/1995 | Swan et al. | |
| 6,080,698 A | 6/2000 | Zhang | |
| 6,106,697 A | 8/2000 | Swan et al. | |
| 2003/0006168 A1 | 1/2003 | Ino et al. | |

FOREIGN PATENT DOCUMENTS

| | | |
|---|---|---|
| CN | 1093101 | 10/1994 |
| CN | 1102431 | 5/1995 |
| CN | 1255474 | 6/2000 |
| CN | 1305445 | 7/2001 |
| EP | 0922744 | 6/1997 |
| EP | 0909804 | 4/1999 |
| EP | 0903178 | 11/2003 |
| JP | 55-162349 | 12/1980 |
| JP | 60-222428 | 11/1985 |
| RU | 2100075 | 12/1997 |
| RU | 2186089 | 7/2002 |

OTHER PUBLICATIONS

English language Abstract of CN 1093101, 2005.
English language Abstract of CN 1255474, Jun. 2000.
English language Abstract of CN 1102431, May 1993.
English language Abstract of CN 1305445, May 1999.
English language Abstract of RUSSIAN 2100075, Dec. 1997.
English language Abstract of JP 55-162349, 1979.
English Language Abstract of RU 2186089, Jul. 27, 2002.

*Primary Examiner*—Thuan Dinh Dang
(74) *Attorney, Agent, or Firm*—Birch, Stewart, Kolasch & Birch, LLP

(57) ABSTRACT

A catalytic conversion process for producing light olefins with a high yield from petroleum hydrocarbons, which comprises the steps of contacting a pre-heated petroleum hydrocarbons feedstock with a catalyst which comprises phosphorus and transition metal modified silica rich zeolite having a structure of pentasil in a riser or a fluidized bed reactor, and converting under the catalytic conversion conditions to produce reaction effluent and a spent catalyst, separating the resulted reaction effluent and spent catalyst, further separating said reaction effluent into liquid products and gaseous products comprising ethylene and propylene; stripping the spent catalyst by steam; regenerating the stripped catalyst by contacting the spent catalyst with oxygen-containing gas and burning off coke; and recycling the regenerated catalyst to reactor for reuse.

11 Claims, No Drawings

CATALYTIC CONVERSION PROCESS FOR PRODUCING LIGHT OLEFINS WITH A HIGH YIELD PETROLEUM HYDROCARBONS

TECHNICAL FIELD

The present invention relates to a catalytic conversion process of petroleum hydrocarbons, in particular, to a catalytic conversion process for producing light olefins with a high yield from petroleum hydrocarbons.

BACKGROUND OF PRESENT INVENTION

The conventional process for producing gaseous olefins from petroleum hydrocarbons is steam cracking process, wherein the feedstocks are light hydrocarbons comprising natural gas, naphtha and light gas oil and so on. The supply of light hydrocarbons was limited as crude oil becomes heavier. Thus, more attentions are paid to processes for producing gaseous olefins from heavy hydrocarbons. Such processes, for example, include thermal cracking process of heavy hydrocarbons by using inert solid materials such as quartz or coke as heat carriers, and thermo-catalytic cracking process of heavy hydrocarbons by using alkali metal oxides or alkaline earth metal oxides as catalyst. The reaction temperatures in such processes are both greater than 800° C.

Recently the processes for producing gaseous olefins from petroleum hydrocarbons have been described in various publications, wherein using solid acidic catalysts in certain reactor style and under certain operation conditions. For example, JP 60-222,428 discloses a process using ZSM-5 as a catalyst and $C_5$ to $C_{25}$ paraffinic hydrocarbons as feedstock The process is carried out at a reaction temperature of between 600 to 750° C., with 30 wt % yield for $C_2$ to $C_4$ olefins. U.S. Pat. No. 3,758,403 disclosed that a catalyst comprising both ZSM-5 zeolite and large pore zeolite (e.g. X type or Y type) as active components in a ratio of 1:10-3:1 raised octane number of gasoline while increasing yield of total propylene and butylenes to about 10 wt %.

It has been reported in U.S. Pat. No. 5,318,696 that the catalyst comprising large pore zeolite and medium pore zeolite in ratio of $SiO_2/Al_2O_3$ being less than 30 can be used to produce high octane gasoline, and to increase the yield of gaseous olefins, especially propylene. Said medium pore zeolite is in the form of MFI structure.

U.S. Pat. No. 4,980,053 disclosed the catalyst comprising mixture of ZSM-5 zeolite and Y type zeolite as active components can be used to increase octane number of gasoline in products and to increase yield of light olefins in reaction temperature of 500~650° C. And light olefins are mainly consisting of propylene and butylene.

It has been reported in prior art that the process for modifying zeolite having a structure of pentasil to increase the selectivity to the reaction product. For example, phosphorus and/or metal ion can be incorporated into zeolite having a structure of pentasil (such as ZSM-5) to adjust the adsorption and catalysis properties of the zeolite.

It has been reported in U.S. Pat. No. 4,365,104 that the process for modifying ZSM-5 zeolite by using phosphorus and magnesium, for the purpose of using modified zeolite to the isomerization of xylene to increase selectivity to xylene. The incorporation of phosphorus and magnesium is to increase the shape selectivity of zeolite. However, both acidity of molecular sieve and hydrocarbons conversion reactivity of zeolite after modification are decreased.

It has been reported in U.S. Pat. No. 5,236,880 that the incorporation of group VIIIB metals, preferably nickel into zeolite in the ratio of $SiO_2$ to $Al_2O_3$ being greater than 5. Said zeolite is in the form of MFI or MEL structure. The catalyst disclosed in U.S. Pat. No. 5,236,880 can be used to increase the conversion of paraffinic hydrocarbons, to increase aromatics content in gasoline fraction, to increase octane number of gasoline in products and yield of gasoline.

A catalyst comprising both phosphorus and rare earth-containing silica rich zeolite having a structure of pentasil as active component has been disclosed in U.S. Pat. No. 5,380,690 and China patent publication 1,093, 101A respectively. The catalyst has stronger hydrothermal stability. The conversion obtained by using said catalyst is higher than that obtained by using the catalyst comprising HZSM-5 zeolite as active component by 4-7 wt % in the reaction temperature of 580° C. Similarly, the yield of $C_2$-$C_4$ olefin is higher by 4~5 wt %.

A combination process of catalytic cracking with dehydrogenation has been disclosed in U.S. Pat. No. 5,414,181. The spent catalyst is regenerated after the catalytic cracking reaction is completed. The regenerated catalyst is deposited with carbon derived from coke precursor and then $C_2$-$C_{10}$ alkane is dehydrogenated to produce olefins.

It has been disclosed in U.S. Pat. No. 6,106,697 that a process for selectively producing $C_2$-$C_4$ olefin by using vacuum gas oil or residual oil as feedstock and using two-stage reactor to carry out catalytic cracking reaction. Vacuum gas oil or residual oil feedstock is fed into the first stage reactor. The feedstock is contacted with large pore zeolite catalyst under conventional catalytic cracking conditions to carry out catalytic cracking reaction to produce various products with different boiling ranges, including gasoline fractions. The gasoline fractions produced in the first reactor are fed into the second reactor and contacted with medium pore zeolite catalyst in the reaction temperature of 500-650° C., the catalyst/oil ratio of 4-10:1, and the oil vapor partial pressure of 70-280 kPa. As a result, $C_2$-$C_4$ olefins are produced.

It has been reported in China patent publication No. 1,255,474A a catalytic cracking process for producing light olefins from lower alkane. The process comprises contacting $C_4$-$C_6$ alkane with a silica rich zeolite catalyst being modified by one of the elements selected from the group consisting of alkali metal, alkaline earth metal and group VIII transition metal and having a structure of pentasil, wherein the catalyst comprises rare earth and phosphorus. The reaction is carried out in temperature of 450-580° C. and weight hourly space velocity of 5-300 hour$^{-1}$. The alkali metal is preferably potassium, alkaline earth metal is preferably barium and group VIII transition metal is preferably iron or nickel.

It has been disclosed in U.S. patent publication No. 2003/0006168A1 that a catalytic cracking process for producing light olefins with a high yield from heavy oil. The process comprises the steps of contacting the heavy oil with a catalyst mixture, consisting of 60 to 95% by weight of a base cracking catalyst containing an USY type molecular sieve and less than 0.5% by weight of rare earth metal oxide, and 5 to 40%. by weight of an additive containing a shape-selective zeolite; the oil and the catalyst are contacted in a downer reactor, and are contacted under conditions so that the reaction zone outlet temperature is in the range of 580-630° C., the catalyst/oil ratio is in the range of 15-40 and the contact time is in the range of 0.1-1.0 seconds. Said process can be used to improve yield of light olefins, for example, the yield of propylene can be about 20% by weight.

It has been disclosed in EP 0,922,744A1 that a process for producing LPG and light olefins with a high yield under the reaction conditions of weight hourly space velocity in the range of 40-120h$^{-1}$, catalyst/oil ratio in the range of 15-25, riser outlet temperature in the range of 530-600° C., reaction pressure in the range of 1.0-4.0 Kg/cm$^2$ g and steam for dilution and quenching of hydrocarbon in the range of 3-50% by weight of the feedstock. The catalyst used in said process comprises 1-6% by weight of USY zeolite, 8-25% by weight of shape-selective zeolite, 0-8% by weight of bottoms selective cracking active component, 0-1% by weight of rare earth component and 60-91% by weight of non-acidic component & binder. The yield of LPG obtained by the process can be about 40-65% by weight. The selectivity of propylene and butylenes in LPG are about 40% and 45% by weight respectively.

The carbon content in the regenerated catalyst is typically required to be less than 0.1% by weight and preferably be less than 0.05% by weight during the catalytic crack process for the purpose of restoring cracking activity of catalyst.

As discussed above, the process for producing light olefins with a high yield by using phosphorus-containing silica rich zeolite having a structure of pentasil as active component has not been described in the prior art, wherein said silica rich zeolite has also been modified with group VIII transition metals, although the processes such as in which silica rich zeolite having a structure of pentasil being used as one of the active components in the catalyst have been disclosed.

DISCLOSURE OF THE INVENTION

The object of present invention is to overcome the disadvantages that are related to the prior art and to provide a catalytic conversion process using a catalyst comprising phosphorus and transition metals modified silica rich zeolite having a structure of pentasil for producing light olefins with a high yield so that more raw materials in petrochemical industry will be produced. Other objects and advantages will be more apparent in view of following detailed description.

In the process of the present invention, pre-heated petroleum hydrocarbons are contacted with a catalyst which comprises phosphorus and transition metal modified silica rich zeolite having a structure of pentasil in a riser or a fluidized bed reactor, and are catalytically converted under given operating conditions to produce reaction effluent and a spent catalyst. The reaction effluents and spent catalyst are separated by a rapid gas-solid separator. The reaction effluents are further separated to obtain ethylene and propylene containing gaseous products and liquid products, and the spent catalyst is removed to a stripper. After stripping, the catalyst is directed to a regenerator, where it is contacted with an oxygen-containing gas and regenerated, the hot regenerated catalyst is recycled to the reactor for reuse.

More particularly, in the process of the present invention, pre-heated petroleum hydrocarbons are contacted with a catalyst which comprises phosphorus and transition metal modified silica rich zeolite having a structure of pentasil in a riser or a fluidized bed reactor at the reaction temperature in the range of 500-700° C., reaction pressure in the range of 150-400 kPa, weight hourly space velocity in the range of 1-200 hour$^{-1}$, catalyst to feedstock ratio by weight in the range of 5-40:1 and steam to feedstock ratio by weight in the range of 0.05-1:1 and catalytically converted. After being stripped and separated from the reaction products, the spent catalyst, having been deposited with coke, is transferred to a regenerator by burning the coke deposited on the catalyst, and returning the catalyst to the reactor. Light olefins, gasoline, diesel, bottoms and other saturated light hydrocarbons are obtained by the separation thereof from the reaction products.

Feedstock and Product

The petroleum hydrocarbons used in present invention as feedstock can be selected from the group consisting of gasoline, atmospheric gas oil, vacuum gas oil, atmospheric residual oil, vacuum residual oil and mixtures thereof, Crude oil also may be directly used. The injection of said feedstock can be either single-site injection or multi-site injection. The term "single-site injection" as used herein means that the petroleum hydrocarbons can be injected into a reactor through the feeding nozzle(s) located in a same elevation. There may be just one feeding nozzle or several feeding nozzles in a reactor. The term "multi-site injection" as used herein means that the petroleum hydrocarbons can be injected into a reactor through the feeding nozzles located in different elevations.

The process according to present invention can be utilized to obtain gaseous products comprising ethylene and propylene and liquid products comprising gasoline and diesel, wherein the yield of ethylene can be about 5-25% by weight and the yield of propylene can be about 21-26% by weight.

Catalyst

In the process according to present invention, the catalyst comprises 0-70% by weight of clay, 5-99% by weight of inorganic oxides and 1-50% by weight of zeolite, all based on total weight of the catalyst. The zeolite comprises 75-100% by weight of silica rich zeolite having a structure of pentasil and 0-25% by weight of Y type zeolite, wherein said silica rich zeolite having a structure of pentasil is modified with both phosphorous and transition metal M, with an anhydrous formula of $(0-0.3)Na_2O.(0.3-5)Al_2O_3.(1.0-10)P_2O_5.(0.7-15)M_xO_y.(0-10)RE_2O_3.(70-98)SiO_2$ based on the mass of oxides. In the formula, element M is at least one element selected from the group consisting of Fe, Co, Ni, Cu, Zn, Mo and Mn. And RE represents rare earth elements, x represents valence of oxygen and y represents valence of transition metal x is equal to 1 and y is a value of the valence of transition metal divided by 2 provided that the valence of transition metal is an even number. It is preferably that said phosphorus and transition metal M modified silica rich zeolite having a structure of pentasil has an anhydrous formula of either $(0-0.2)Na_2O.(0.9-5)Al_2O_3.(1.5-7)P_2O_5.(0.9-10)M_xO_y.(82-92)SiO_2$, or $(0-0.2)Na_2O.(0.9-5)Al_2O_3.(1.5-7)P_2O_3.(0.9-10)M_xO_y.(0.5-10)RE_2O_3.(82-92)SiO_2$ based on the mass of oxides.

The transition metal M have the function of dehydrogenation, and are preferably at least two elements or more selected from the group consisting of Fe, Co, Ni, Cu, Zn, Mo and Mn, more preferably selected from the group consisting of Fe, Co and Ni, and the most preferably are Fe and Ni.

The clay comprised in the catalyst according to present invention can be natural source or synthesized source. The clay can be any conventional one used as matrix of cracking catalyst in the art, which can be optionally subjected to various chemical and/or physical treatments. Examples of such clays are, but not limited to, kaolin or kaolin polyhydrate and the like.

The inorganic oxides comprised in the catalyst according to present invention can be selected from the group consisting of amorphous $SiO_2Al_2O_3$, $Al_2O_3$ and/or $SiO_2$.

The Y type zeolite comprised in the catalyst according to present invention can be prepared by using various chemical and/or physical methods. Such methods include, for example, hydrothermal method, chemical treatment method (such as treated by EDTA acid, by ammonium fluorosilicate to extract aluminum and reinforce silicon, and $SiCl_4$ gas phase process) or the combination thereof. Y type zeolite optionally contains rare earth elements. The rare earth element-containing Y type zeolite is referred as rare earth hydrogen Y (REHY) or rare earth ultra-stable Y (REUSY).

In general, the preparation of said silica rich zeolite having a structure of pentasil includes the steps of ammonium exchange, modification by phosphorus and metals, and calcination.

The ammonium exchange can be as follows: sodium type silica rich zeolite having a structure of pentasil and optionally comprising rare earth elements obtained by conventional crystallization is exchanged in a ratio of zeolite: ammonium salt: $H_2O$ in 1:(0.1-1):(5-10) by weight in a temperature from room temperature to 100° C. for a period of 0.3-1 hour and then filtered, wherein template agent should be initially removed if an organic template agent has been used during the synthesis of sodium type zeolite. Said ammonium salt can be conventional inorganic one in the art and can be selected from the group consisting of ammonium chloride, ammonium nitrate, ammonium sulfate or the mixture thereof.

The modification by phosphorus and metals can be carried out by impregnation or ion exchange methods.

The impregnation methods may include, for example, as follows:
a. ammonium exchanged zeolite is mixed homogeneously with a pre-calculated amount of aqueous solution containing phosphorus compound in a temperature from room temperature to 95° C., dried, then calcined in a temperature of 400-800° C., and then mixed homogeneously with a pre-calculated amount of aqueous solution containing transition metal M compound in a temperature from room temperature to 95° C. and dried.
b. ammonium exchanged zeolite is mixed homogeneously with a pre-calculated amount of aqueous solution containing phosphorus compound in a temperature from room temperature to 95° C., dried, and then mixed homogeneously with a pre-calculated amount of aqueous solution containing transition metal M compound in a temperature from room temperature to 95° C., and dried, The order for impregnating into said aqueous solutions can be reversed.
c. ammonium exchanged zeolite is mixed homogeneously with pre-calculated amounts of aqueous solution mixture containing phosphorus and transition metal M compounds in a temperature from room temperature to 95° C., and then dried.

The ion exchange method can be as follows: ammonium exchanged zeolite is mixed homogeneously with a pre-calculated amount of aqueous solution containing phosphorus compound in a temperature from room temperature to 95° C., dried, then calcined in a temperature of 400-800° C., and then mixed homogeneously with a pre-calculated amount of aqueous solution containing transition metal M compound in a ratio of solid to liquid of 1:(5-20), mixed in a temperature of 80-95° C. under pH 4-7 for 2-3 hours and then filtered. The exchange can be repeated for several times. Resulted product is washed with water and then dried.

The phosphorus compound containing aqueous solution can be the aqueous solution of the phosphoric acid, aluminum phosphate, ammonium hydrogen phosphate, ammonium biphosphate, ammonium phosphate and the mixture thereof. The transition metal M compound containing aqueous solution can be the aqueous solution of chloride, nitrate, sulfate or carbonate of the transition metal M, for example, but not be limited to, iron sulfate, ferrous sulfate, iron nitrate, iron chloride, ferrous chloride, cobalt sulfate, cobalt nitrate, cobalt chloride, nickel nitrate, nickel sulfate, nickel chloride and the like.

The catalyst according to present invention can be prepared by the steps of mixing the precursor of inorganic oxides such as pseudo-boehmite, alumina sol, silica sol or its mixture, and silica-alumina sol or gel with kaolin polyhydrate in a pre-determined ratio; formulating a slurry with the solid content of 10-50 wt % by adding de-cationized water and then homogeneously mixed, adjusting and maintaining the pH value of the slurry to 2-4 by using an inorganic acid such as hydrochloric acid, nitric acid, phosphoric acid or sulfuric acid, adding alumina sol after aging statically at temperature of 20-80° C. for 0-2 hours, mixing for 0.5-1.5 hours, adding into it pre-calculated amounts of both silica rich zeolite having a structure of pentasil and Y type zeolite, homogenizing, spray drying, washing off the free sodium ion and drying.

Other Matters

In the process according to present invention, it is preferred that the petroleum hydrocarbons are contacted with hot catalyst having a carbon content of 0-0.5% by weight, preferably 0.05-0.45% by weight in a riser or fluidized bed reactor. More preferably the carbon content is in the range of 0.1-0.3% by weight. The catalyst comprises phosphorus and transition metal M modified silica rich zeolite having a structure of pentasil. The catalytic conversion reaction is carried out subsequently. The carbon-containing catalyst as described above can be prepared by controlling the regenerate condition of the spent catalyst. In another word, the spent catalyst is regenerated in regenerator by using the part combustion operation. Alternatively, the carbon-containing catalyst can be prepared by contacting the regenerated catalyst with light hydrocarbons enriched by olefins in a pre-reactor before said regenerated catalyst is recycled to reactor. The pre-reactor as used herein can be either a second riser or fluidized bed reactor other than the reactor for catalytic conversion of petroleum hydrocarbons, or a portion zone in the reactor for catalytic conversion, for example, the reaction zone on the bottom of riser reactor.

In the process according to present invention, it is preferable to strip the regenerated catalyst with steam and/or light hydrocarbons enriched by methane to remove non-hydrocarbon gaseous impurities absorbed on or carried by the catalyst, and then recycle the catalyst to reactor.

The examples as described follows will further illustrate the process according to present invention, but not intend to limiting present invention in any way. The catalysts used in the examples and comparative Examples respectively are as follows.

EXAMPLES

Catalyst A is one of the catalysts being prepared according to present invention, which comprises 18% silica rich zeolite having a structure of pentasil, 27% aluminum oxide and the balance being kaolin, based on total weight of catalyst.

Silica rich zeolite having a structure of pentasil comprises 2.4% phosphorus oxide, 3.8% rare earth oxide, and 1.5% iron oxide based on total weight of zeolite, with a mole ratio of silica to alumina being 30.

Catalyst B is another one of the catalysts being prepared according to present invention, which comprises 18% silica rich zeolite having a structure of pentasil, 27% aluminum oxide and the balance being kaolin, based on total weight of catalyst. Silica rich zeolite having a structure of pentasil comprises 4.1% phosphorus oxide, 1.0% iron oxide and 1.0% nickel oxide based on total weight of zeolite, with a mole ratio of silica to alumina being 60.

Catalyst C is another one of the catalysts being prepared according to present invention, which comprises 15% silica rich zeolite having a structure of pentasil, 5% REHY zeolite, 20% aluminum oxide, 6% amorphous aluminum silicate and the balance being kaolin, based on total weight of catalyst. Silica rich zeolite having a structure of pentasil comprises 2.1% phosphorus oxide and 1.0% iron oxide based on total weight of zeolite, with a mole ratio of silica to alumina being 60.

Catalyst D is another one of the catalysts being prepared according to present invention, which comprises 15% silica rich zeolite having a structure of pentasil, 5% REHY zeolite, 20% aluminum oxide, 6% amorphous aluminum silicate and the balance being kaolin, based on total weight of catalyst. Silica rich zeolite having a structure of pentasil comprises 2.1% phosphorus oxide, 1.0% iron oxide and 0.6% nickel oxide based on total weight of zeolite, with a mole ratio of silica to alumina being 60.

Comparative catalyst A is prepared by similar formulation and method as that described for catalyst A, except the silica rich zeolite having a structure of pentasil comprises 2.4% phosphorus oxide and 3.8% rare earth oxide based on total weight of zeolite, with a mole ratio of silica to alumina being 30.

Comparative catalyst B is prepared by similar formulation and method as that described for catalyst B, except the silica rich zeolite having a structure of pentasil comprises 4.1% phosphorus oxide based on total weight of zeolite, with a mole ratio of silica to alumina being 60.

Comparative catalyst C is prepared by similar formulation and method as that described for catalyst C, except the silica rich zeolite having a structure of pentasil is HZSM-5 zoelite with a mole ratio of silica to alumina being 60.

Example 1

The example illustrates that ethylene and propylene are produced by the process according to present invention in which catalyst A comprising silica rich zeolite having a structure of pentasil is used, wherein the zeolite has been modified by phosphorus, rare earth and iron.

A catalytic conversion reaction is carried out in a bench-scale fixed-fluidized bed reactor with vacuum gas oil feedstock having density of 0.873 and boiling-range of 350-540° C., under operation conditions of reaction temperature of 700° C., catalyst/oil ratio of 25:1, steam/oil ratio of 0.5:1 and weight hourly space velocity of 10 h$^{-1}$. The results are shown in table 1.

Comparative example 1

The comparative example illustrates the use of comparative catalyst A comprising phosphorus and rare earth modified silica rich zeolite having a structure of pentasil. The feedstock and operation conditions are both same to that described in example 1. The results are shown in table 1.

TABLE 1

| | Catalyst | |
|---|---|---|
| Distribution of products, wt % | Catalyst A | Comparative catalyst A |
| Cracked gas | 70.58 | 69.86 |
| In which, Ethylene | 25.23 | 23.82 |
| Propylene | 21.56 | 19.85 |
| Butylenes | 5.23 | 6.86 |
| Gasoline | 11.63 | 12.16 |
| Diesel | 3.61 | 3.77 |
| Bottoms | 3.06 | 3.13 |
| Coke | 11.12 | 11.08 |
| Yield of total gaseous olefins, wt % | 52.02 | 50.53 |

Example 2

The example illustrates that ethylene and propylene are produced by the process according to present invention in which catalyst B comprising silica rich zeolite having a structure of pentasilis is used, wherein the zeolite has been modified by phosphorus, iron and nickel.

A catalytic conversion reaction is carried out in a bench-scale fixed-fluidized bed reactor with vacuum gas oil feedstock having density of 0.873 and boiling-range of 350~540° C., under operation conditions of reaction temperature of 620° C., catalyst/oil ratio of 15:1, steam/oil ratio of 0.4:1 and weight hourly space velocity of 150 h$^{-1}$. The results are shown in table 2.

Comparative Example 2

The comparative example illustrates the use of comparative catalyst B comprising phosphorus modified silica rich zeolite having a structure of pentasil. The feedstock and operation conditions are both same to that described in example 2. The results are shown in table 2.

TABLE 2

| | Catalyst | |
|---|---|---|
| Distribution of products, wt % | Catalyst B | Comparative catalyst B |
| Cracked gas | 66.45 | 65.66 |
| In which, Ethylene | 16.02 | 15.23 |
| Propylene | 25.81 | 24.35 |
| Butylenes | 12.02 | 11.87 |
| Gasoline | 15.88 | 16.24 |
| Diesel | 5.42 | 5.63 |
| Bottoms | 4.47 | 4.68 |
| Coke | 7.78 | 7.79 |
| Yield of total gaseous olefins, wt % | 53.85 | 53.85 |

Example 3

The example illustrates that ethylene and propylene are produced by the process according to present invention in which catalyst C comprising both silica rich zeolite having a structure of pentasil and REUSY zeolite is used, wherein the silica rich zeolite has been modified by phosphorus and iron. Further, catalyst D comprising both silica rich zeolite having a structure of pentasil and REUSY zeolite is used, wherein the silica rich zeolite has been modified by phosphorus, iron and nickel.

Catalytic conversion reactions are carried out in a bench-scale fixed-fluidized bed reactor with vacuum gas oil feedstock having density of 0.873 and boiling-range of 350~540° C., under operation condition of reaction temperature of 550° C., catalyst/oil ratio of 10:1, steam/oil ratio of 0.3;1 and weight hourly space velocity of 250 $h^{-1}$. The results are shown in table 3.

Comparative Example 3

The comparative example illustrates the use of comparative catalyst C comprising both ZSM-5 zeolite and REUSY zeolite. The feedstock and operation conditions are both same to that described in example 3. The results are shown in table 3.

TABLE 3

| | Catalyst | | |
|---|---|---|---|
| Distribution of products, wt % | Catalyst C | Catalyst D | Comparative catalyst C |
| Cracked gas | 54.28 | 55.36 | 51.83 |
| In which, Ethylene | 4.96 | 5.17 | 4.15 |
| Propylene | 23.08 | 23.84 | 21.37 |
| Butylenes | 14.38 | 14.87 | 14.56 |
| Gasoline | 28.59 | 27.37 | 30.56 |
| Diesel | 7.16 | 7.19 | 7.38 |
| Bottoms | 5.45 | 5.48 | 5.55 |
| Coke | 4.52 | 4.60 | 4.68 |
| Yield of total gaseous olefins, wt % | 42.42 | 43.88 | 40.08 |

Example 4

The example illustrates that the catalytic conversion of petroleum hydrocarbons to produce light olefins in fluidized bed reactor by using the process according to present invention.

A catalytic conversion reaction is carried out in a pilot fluidized bed reactor operated in the continuous reaction-regeneration mode with catalyst A and paraffin-based atmospheric residual oil feedstock having density of 0.896. The hot regenerated catalyst is contacted with a portion of C4 fraction which have been recycled to the pre-lifting zone located in the bottom of fluidized bed reactor in elevated temperature so that about 0.18% by weight of carbon is deposited onto the catalyst. The coke-deposited catalyst is contacted with feedstock which has been heated to about 350° C. by means of pre-heated oven in the fluidized bed reactor under the conditions of reactor bed temperature of 580° C., pressure of 200 kPa, weight hourly space velocity of 4 $h^{-1}$, catalyst/oil ratio of 15:1 and steam/oil ratio of 0.25:1. The reaction effluents and spent catalyst are transferred to a gas-solid separator through reactor outlet. The reaction effluents and spent catalyst are rapidly separated between each other in the gas-solid separator. The reaction effluents are further separated into gaseous products comprising ethylene and propylene, C4 fraction, gasoline, diesel, bottoms and the like. The spent catalyst is forwarded to stripper by the action of gravity, and hydrocarbon products absorbed onto the spent catalyst are stripped from catalyst particles by using steam. The stripped spent catalyst is transferred to a regenerator in which catalyst is contacted with hot air to regenerate. The regenerated catalyst is recycled to the pre-lifting zone located in the bottom of fluidized bed reactor in which catalyst is contacted with C4 fraction to deposit the catalyst with coke. The coke-deposited catalyst is contacted with feedstock and the reaction is continued. The results are shown in table 4.

Comparative Example 4

The comparative example illustrates that the production of light olefins by using the process disclosed in the art under same operation conditions to that described in example 4.

A catalytic conversion reaction is carried out in a pilot fluidized bed reactor operated in the continuous reaction-regeneration mode with comparative catalyst A and paraffin-based atmospheric residual oil feedstock having density of 0.896. The reaction is in single pass operation mode. Regenerated catalyst is contacted with feedstock which has been heated to about 350° C. by means of pre-heated oven in the fluidized bed reactor under the conditions of reactor bed temperature of 580° C., pressure of 200 kPa, weight hourly space velocity of 4 $h^{-1}$, catalyst/oil ratio of 15:1 and steam/oil ratio of 0.25:1. The reaction effluents and spent catalyst are transferred to a gas-solid separator through reactor outlet. The reaction effluents and catalyst are rapidly separated between each other in the gas-solid separator. The reaction effluents are further separated into light gaseous products comprising ethylene and propylene, C4 fraction, gasoline, diesel, bottoms and the like. The spent catalyst is forwarded to stripper by the action of gravity, and hydrocarbon products absorbed onto the spent catalyst are stripped from catalyst particles by using steam. The stripped spent catalyst is transferred to a regenerator in which catalyst is contacted with hot air to regenerate The resulted regenerated catalyst has a carbon content of less than 0.05% by weight. The regenerated catalyst is recycled to fluidized bed reactor and the reaction is continued. The results are shown in table 4.

TABLE 4

| Distribution of products, wt % | Example 4 | Comparative example 4 |
|---|---|---|
| Cracked gas | 54.74 | 53.40 |
| In which, Ethylene | 6.92 | 6.76 |
| Propylene | 23.54 | 21.68 |
| Butylenes | 14.89 | 16.37 |
| Gasoline | 18.83 | 20.59 |
| Diesel | 8.82 | 8.76 |
| Bottoms | 7.99 | 7.87 |
| Coke | 9.62 | 9.45 |
| Yield of total gaseous olefins, wt % | 45.35 | 44.81 |

Example 5

The example illustrates that the catalytic conversion of petroleum hydrocarbons to produce light olefins in riser reactor by using the process according to present invention.

A catalytic conversion reaction is carried out in a pilot riser reactor operated in the continuous reaction-regeneration mode with catalyst C and paraffin-based atmospheric residual oil feedstock having density of 0.896. The reaction-regeneration is in a part combustion regeneration operation mode. The resulted regenerated catalyst has a carbon content of 0.2% by weight. The steps comprise contacting the coke-deposited catalyst with feedstock which has been heated to about 350° C. by means of pre-heated oven in the reactor under the conditions of reactor outlet temperature of 650° C., pressure of 250 kPa, reaction time of 5 seconds, catalyst/oil ratio of 25;1 and steam/oil ratio of 0.5:1. The reaction effluents and spent catalyst are transferred to a gas-solid separator through reactor outlet. The reaction effluents and catalyst are rapidly-separated between each other in the gas-solid separator. The reaction effluents are further separated into gaseous products, gasoline, diesel, bottoms and the like. The spent catalyst is forwarded to stripper by the action of gravity, and hydrocarbon products absorbed onto the spent catalyst are stripped from catalyst particles by using steam. The stripped spent catalyst is transferred to a regenerator in which catalyst is contacted with hot air to regenerate. The carbon content in the regenerated catalyst is adjusted to 0.2 wt % by controlling regenerate temperature and air rate. The coke-deposited regenerated catalyst is recycled into reactor. The results are shown in table 5.

Comparative Example 5

The comparative example illustrates that the production of light olefins by using the process disclosed in the art under same operation conditions to that described in example 5.

A catalytic conversion reaction is carried out in a pilot riser reactor operated in the continuous reaction-regeneration mode with comparative catalyst C and paraffin-based atmospheric residual oil feedstock having density of 0.896. The reaction is in a full combustion regeneration operation mode. Regenerated catalyst is contacted with feedstock which has been heated to about 350° C. by means of pre-heated oven in the reactor under the conditions of reactor outlet temperature of 650° C., pressure of 250 kPa, reaction time of 5 seconds, catalyst/oil ratio of 25:1 and steam/oil ratio of 0.5:1. The reaction effluents and spent catalyst are transferred to a gas-solid separator through reactor outlet. The reaction effluents and catalyst are rapidly separated between each other in the gas-solid separator. The reaction effluents are further separated into gaseous products, gasoline, diesel, bottoms and the like. The spent catalyst is forwarded to stripper by the action of gravity, and hydrocarbon products absorbed onto the spent catalyst are stripped form catalyst particles by using steam. The stripped spent catalyst is transferred to a regenerator in which catalyst is contacted with hot air to regenerate. The resulted regenerated catalyst has a carbon content of less than 0.05% by weight. The regenerated catalyst is recycled into reactor. The results are shown in table 5.

TABLE 5

| Distribution of products wt % | Example 5 | Comparative example 5 |
|---|---|---|
| Cracked gas | 70.72 | 66.88 |
| In which, Ethylene | 24.36 | 21.67 |
| Propylene | 22.84 | 18.36 |
| Butylenes | 10.06 | 8.25 |
| Gasoline | 10.76 | 14.96 |
| Diesel | 6.26 | 6.17 |
| Bottoms | 2.84 | 2.74 |
| Coke | 9.42 | 9.25 |
| Yield of total gaseous olefins gas, wt % | 57.26 | 48.28 |

It can be seen from the results cited in tables 1-5, the yield of total gaseous olefins according to the process of present invention is greater than that according to the process of comparative examples, especially the yield of ethylene and propylene.

The present application claims priority under 35 U.S.C. §119 of CN 03147977.4 filed on Jun. 30, 2003 and CN 03147978.2 filed on Jun. 30, 2003. The disclosures of the foregoing application are expressly incorporated by reference herein in its entirety.

What is claimed is:

1. A catalytic conversion process for producing light olefins with a high yield from petroleum hydrocarbons, which comprises the steps of:
   contacting a pre-heated petroleum hydrocarbons feedstock with a catalyst which comprises phosphorus and transition metal modified silica rich zeolite, wherein said transition metal is at least one element selected from the group consisting of Fe, Co, Ni, Cu, Zn, Mo, and Mn, having a structure of pentasil in a riser or a fluidized bed reactor, and converting under the catalytic conversion conditions to produce reaction effluent and a spent catalyst,
   separating the resulted reaction effluent and spent catalyst, further separating said reaction effluent into liquid products and gaseous products comprising ethylene and propylene;
   stripping the spent catalyst by steam;
   regenerating the stripped catalyst by contacting the spent catalyst with oxygen-containing gas and burning off coke;
   contacting the regenerated catalyst with light hydrocarbons enriched by olefins in a pre-reactor, wherein the pre-reactor is either a second riser or fluidized bed reactor other than the reactor for catalytic conversion of petroleum hydrocarbons or a portion zone in the reactor for catalytic conversion of petroleum hydrocarbons, and said catalyst has a carbon content of 0.1 -0.3% by weight; and
   recycling the regenerated catalyst to reactor for reuse.

2. The process according to claim 1, wherein said process is carried out under catalytic conversion conditions of reaction temperature in the range of 500-700° C., reaction pressure in the range of 150-400 kPa, weight hourly space velocity in the range of 1-200 hour$^{-1}$, catalyst to feedstock ratio by weight in the range of 5-40:1 and steam to feedstock ratio by weight in the range of 0.05-1:1.

3. A The process according to claim 2, wherein said process is carried out under catalytic conversion conditions of reaction temperature in the range of 550-650° C., weight hourly space velocity in the range of 4-180 hour$^{-1}$, catalyst to feedstock ratio by weight in the range of 10-30:1 and steam to feedstock ratio by weight in the range of 0.1-0.5:1.

4. The process according to claim 1, wherein said petroleum hydrocarbons feedstock is selected from the group consisting of: gasoline, atmospheric gas oil, vacuum gas oil, atmospheric residual oil, vacuum residual oil, crude oil and a mixture thereof; and the injection of said petroleum hydrocarbons is either single-site injection or multi-site injection.

5. The process according to claim 1, wherein said phosphorus and transition metal modified silica rich zeolite having a structure of pentasil has an anhydrous formula of $(0\text{-}0.3)Na_2O$ $(0.3\text{-}5)Al_2O_3\text{-}(1.0\text{-}10)$ $P_2O_5(07\text{-}15)M_xO_y(0\text{-}10)$ $RE_2O_3$ $(70\text{-}98)SiO_2$ based on the mass of oxides, wherein M is one or more elements selected from the group consisting of Fe, Co, Ni, Cu, Zn, Mo and Mn, RE represents rare earth elements, x represents the valence of oxygen, and y represents the valence of the transition metal.

6. The process according to claim 5, wherein said phosphorus and transition metal modified silica rich zeolite having a structure of pentasil has an anhydrous formula of either $(0\text{-}0.2)Na_2O(0.9\text{-}5)Al_2O_3(1.5\text{-}7)P_2O_5(0.9\text{-}10)M_xO_y(82\text{-}92)SiO_2$ based on the mass of oxides, or $(0\text{-}0.2)Na_2O (0.9\text{-}5)Al_2O_3(1.5\text{-}7)P_2O_5(0.9\text{-}10)M_xO_y,$ $(0.5\text{-}10)RE_2O_3(82\text{-}92)SiO2$ based on the mass of oxides, wherein M, x and y are as defined in claim 5.

7. The process according to claim 5, wherein M is at least two elements or more selected from the group consisting of Fe, Co, Ni, Cu, Zn, Mo and Mn.

8. The process according to claim 7, wherein M is at least two elements or more selected from the group consisting of Fe, Co and Ni.

9. The process according to claim 8 wherein M is Fe and Ni.

10. The process according to claim 1 wherein said catalyst comprising phosphorus and transition metal modified silica rich zeolite having a structure of pentasil is obtained by regenerating the spent catalyst in a regenerator which operates in a part combustion mode, wherein said catalyst has a carbon content of 0.1-0.3% by weight.

11. The process according to claim 1, wherein said regenerated catalyst is stripped with steam and/or with light hydrocarbons enriched by methane to remove non-hydrocarbon gaseous impurities absorbed on and/or carried by the catalyst, and then the catalyst is recycled for reuse.

* * * * *